United States Patent [19]

Baker et al.

[11] 4,119,433

[45] Oct. 10, 1978

[54] 3-HALO-5-(LOWER ALKOXY) PHENOXY ALKYL AMIDES

[75] Inventors: Don R. Baker, Orinda; Francis H. Walker, Mill Valley, both of Calif.

[73] Assignee: Stauffer Chemical Company, Westport, Conn.

[21] Appl. No.: 812,957

[22] Filed: Jul. 5, 1977

[51] Int. Cl.² ............ A01N 9/20; C07C 121/66; C07C 103/22
[52] U.S. Cl. .................... 71/118; 71/105; 260/465 D; 260/559 B
[58] Field of Search .......... 71/118; 260/559 B

[56] References Cited

U.S. PATENT DOCUMENTS

| | | | |
|---|---|---|---|
| 2,412,510 | 12/1946 | Jones | 71/118 |
| 2,927,126 | 3/1960 | Pursglove | 260/465 D |
| 2,948,754 | 8/1960 | Litvan et al. | 260/559 B |
| 3,007,962 | 11/1961 | Metivier | 260/559 B X |
| 3,012,936 | 12/1961 | Stoll et al. | 260/559 B X |
| 3,044,931 | 7/1962 | Holstius | 260/559 B X |
| 3,272,844 | 9/1965 | Easton et al. | 260/559 B X |
| 3,439,018 | 4/1969 | Brookes et al. | 71/105 X |
| 3,900,308 | 8/1975 | Poignant et al. | 71/118 |
| 3,932,168 | 1/1976 | Stein et al. | 71/105 |
| 3,953,507 | 4/1976 | Baker et al. | 260/559 B |
| 4,001,430 | 1/1977 | Baker et al. | 260/559 B X |
| 4,014,679 | 3/1977 | Perronnet et al. | 260/559 B |
| 4,051,184 | 9/1977 | Arneklev et al. | 260/559 B |

Primary Examiner—Joseph Paul Brust
Attorney, Agent, or Firm—Joel G. Ackerman

[57] ABSTRACT

Compounds having the formula

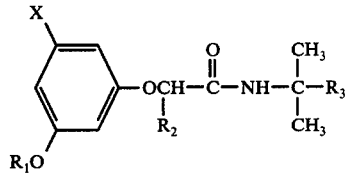

in which X is a halogen, $R_1$ is lower alkyl, $R_2$ is lower alkyl, and $R_3$ is lower alkyl, lower alkynyl, or cyano. The compounds have been found to have utility as herbicides, particularly as pre-emergence herbicides.

11 Claims, No Drawings

3-HALO-5-(LOWER ALKOXY) PHENOXY ALKYL AMIDES

SUMMARY OF THE INVENTION

This invention relates to novel herbicidal compounds having the formula

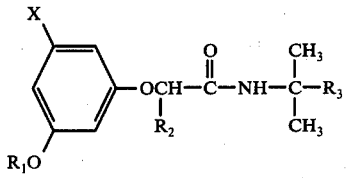

in which X is a halogen, $R_1$ is lower alkyl, $R_2$ is lower alkyl, and $R_3$ is lower alkyl, lower alkynyl or cyano.

By the term "lower alkyl" is meant such groups having from 1 to 4 carbon atoms, for example, methyl, ethyl, and the various propyl and butyl moieties. By the term "lower alkynyl" is meant such groups having from 2 to 4 carbon atoms and one triple bond, such as ethynyl, propynyl, and butynyl. The term "halogen" includes, for example, chloro, bromo and iodo. Of the halogens, chloro is preferred.

The compounds of this invention have been found, in general, to be active herbicides; that is, they have been found to be herbicidally effective against various weeds. In the broadest sense, weeds are plants which grow in locations in which they are not desired. The compounds of this invention have varied herbicidal activities against weeds, according to the particular structure of the compound. In general, as can be seen in the data which follows, these compounds have been found to have greater activity as pre-emergence herbicides, although they also show activity as post-emergence herbicides.

As defined herein, an herbicide means a compound which controls or modifies the growth of plants. By the term "herbicidally effective amount" is meant an amount of a compound which causes a modifying effect upon the growth of plants. By "plants" is meant germinant seeds, emerging seedlings and established vegetation, including roots and above-ground portions. Such modifying effects include all deviations from development, for example killing, retardation, defoliation, desiccation, regulation, stunting, tillering, stimulation, leaf burn, dwarfing, and the like.

Therefore, in another aspect, this invention relates to herbicidal compositions of matter employing the compounds of the present invention in admixture with an inert diluent or carrier. In another aspect, this invention relates to a method for controlling undesirable vegetation comprising applying to such vegetation or the locus thereof an herbicidally effective amount of a compound of the present invention. In a preferred embodiment of this aspect, the compound is applied prior to the emergence of the undesirable vegetation at the locus.

In general, the compounds of the present invention can be prepared by reacting an appropriate phenol with a halo-substituted aliphatic acid to produce a corresponding phenoxy-substituted alkanoic acid (reaction a). This acid is then reacted with phosgene (reaction b) to produce the corresponding acyl chloride, which is then reacted with an amine in the presence of triethylamine or a similar base to produce the desired product (reaction c):

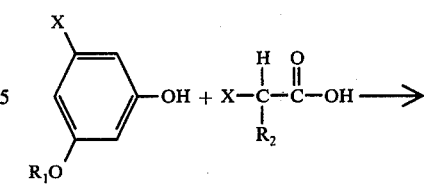

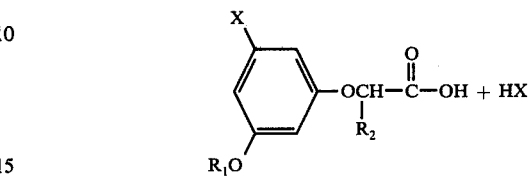

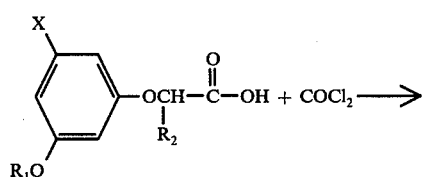

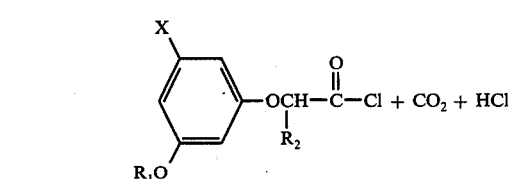

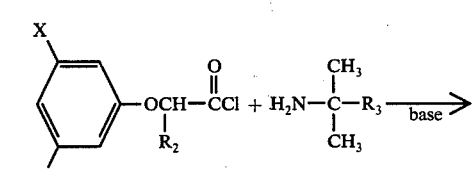

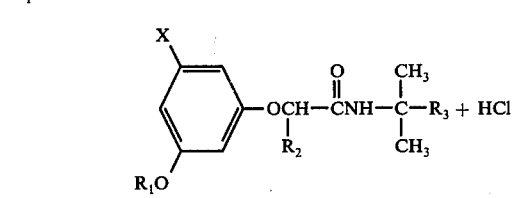

The following represents an example of the preparation of a compound of the present invention.

EXAMPLE 1

Preparation of N-(1,1-dimethylpropynyl)-2-(3-chloro-5-methoxy)-phenoxybutyramide (Compound 1 herein).

a. A mixture of 50 g. (0.32 moles) 3-chloro-5-methoxyphenol and 63.2 g. (0.38 mole) 2-bromobutyric acid was placed in a 500 ml. flask and 60.8 g. (0.79 moles) 50% sodium hydroxide was added slowly with rapid stirring below 50° C. with cooling. The mixture was heated to 90° C. at the conclusion of the addition and maintained at 90° C. for ½ hour. The mixture was next cooled to room temperature and the pH adjusted to 2 with concentrated HCl. A solid separated which was extracted with 400 ml. ether. The ether extract was washed with 100 ml. water and dried over magnesium sulfate. Evaporation of the solvent left a solid which was recrystallized from cyclohexane to give 54.0 g. of 2-(3-chloro-5-methoxy)phenoxy butyric acid, m.p. 96° – 99° C.

b. A mixture of 54 g. (0.22 moles) of the compound prepared in step (a), 0.2 ml. dimethylformamide and 50 ml. benzene was placed in a 300 ml. flask. The mixture was heated to 55° – 60° C. and phosgene was then introduced at a rate such that there was a steady evolution of hydrogen chloride and carbon dioxide. Phosgene addition was continued until 31 g. (0.3 moles) had been added. The solution was then cooled to room temperature and the solvent was removed in vacuum to leave 58.8 g. of the acid chloride, an oil, $n_D^{30}$ 1.5280.

c. A mixture of 4.4 g. (0.05 moles) dimethylpropargylamine and 5.4 g. (0.05 moles) triethylamine in 75 ml. benzene was placed in a 300 ml. flask. A solution of the acid chloride from step (b) in 15 ml. benzene was added to the amine mixture, slowly with rapid stirring. The temperature rose to 50° C. over the course of the addition. At the completion of the addition, the mixture was allowed to return to room temperature and was then washed with 100 ml. water, 100 ml. dilute hydrocarbonic acid, 100 ml. 5% sodium carbonate solution and 100 ml. water. The solution was dried over magnesium sulfate and evaporated to leave 13.2 g. of the desired compound m.p. 54° – 58° C.

The following Table I lists some representative compounds of this invention:

TABLE I $$\underset{R_1O}{\underset{\displaystyle |}{\text{X}}}\!\!\!\diagdown\!\!\!\bigcirc\!\!\!\diagup\!\!\!-\text{OCH}\underset{R_2}{\underset{\displaystyle |}{}}-\overset{O}{\overset{\displaystyle \|}{C}}-\text{NH}-\underset{CH_3}{\underset{\displaystyle |}{\overset{CH_3}{\overset{\displaystyle |}{C}}}}-R_3$$

| Compound No. | X | $R_1$ | $R_2$ | $R_3$ | m.p., ° C |
|---|---|---|---|---|---|
| 1 | Cl | $CH_3$ | $C_2H_5$ | C≡CH | 54 – 58 |
| 2 | Cl | $CH_3$ | $C_2H_5$ | C≡N | 101–103 |
| 3 | Cl | $CH_3$ | $C_2H_5$ | $CH_3$ | 85 – 89 |

Herbicidal Screening Tests

The representative compounds in the foregoing Table I were tested as herbicides in the following manner:

A. Pre-emergence Herbicide Screening Test

Using an analytical balance, 20 mg. of the compound to be tested was weighed out on a piece of glassine weighing paper. The paper and compound were placed in a 30 ml. wide-mouth bottle and 3 ml. of acetone containing 1% polyoxyethylene sorbitan monolaurate emulsifier was added to dissolve the compound. If the material was not soluble in acetone, another solvent such as water, alcohol or dimethylformamide (DMF) was used instead. When DMF was used, only 0.5 ml. or less was used to dissolve the compound and then another solvent was used to make the column up to 3 ml. The 3 ml. solution was sprayed uniformly on the soil contained in a polystyrene flat 7 inches long, 5 inches wide and 2.75 inches deep, one day after planting weed seeds. A No. 152 DeVilbiss atomizer was used to apply the spray using compressed air at a pressure of 5 lb./sq. in. The rate of application was 8 lb./acre and the spray volume was 143 gal./acre.

On the day preceeding treatment, the flat was filled to a depth of 2 inches with loamy sand soil. Seeds of seven different weed species were planted in individual rows using one species per row across the width of the flat. The seeds were covered with soil so that they were planted at a depth of 0.5 inch. The seeds used were hairy crabgrass (*Digitaria sanguinalis*), yellow foxtail (*Setaria glauca*), watergrass (*Echinochloa crusgalli*), red oat (*Avena sativa*), redroot pigweed (*Amaranthus retroflexus*), Indian mustard (*Brassica juncea*), and curly dock (*Rumex crispus*). Ample seeds were planted to give about 20 to 50 seedlings per row after emergence depending on the size of the plants.

After treatment, the flats were placed in the greenhouse at a temperature of 70° to 85° F. and watered by sprinkling. Two weeks after treatment the degree of injury or control was determined by comparison with untreated check plants of the same age. The injury rating from 0 to 100% was recorded for each species as percent control with 0% representing no injury and 100% representing complete kill.

B. Post-emergence Herbicide Screening Test

Seeds of six plant species, including hairy crabgrass, watergrass, red oat, mustard, curly dock and pinto beans (*Phaseolus vulgaris*) were planted in flats similar to those used above for pre-emergence screening. The flats were placed in the greenhouse at 70° to 85° F. and watered daily with a sprinkler. About 10 to 14 days after planting when the primary leaves of the bean plants were almost fully expanded and the first trifoliate leaves were just starting to form, the plants were sprayed. The spray was prepared by weighing out 20 mg. of the test compound, dissolving it in 5 ml. of acetone containing 1% polyoxyethylene sorbitan monolaurate emulsifier and then adding 5 ml. of water. The solution was sprayed on the foliage using a No. 152 DeVilbiss atomizer at an air pressure of 5 lb./sq. in. The spray concentration was 0.2% and the rate was 8 lb./acre. The spray volume was 476 gal./acre. Injury ratings are given in Table II.

Table II

| Compound No. | Pre-emergence Control* | Post-emergence Control* |
|---|---|---|
| 1 | 90 | 72 |
| 2 | 81 | 28 |
| 3 | 84 | 57 |

*average of plants tested.

In practice, the compounds are formulated with an inert carrier, utilizing methods well known to those skilled in the art, thereby making them suitable for application as dusts, sprays, or drenches and the like, in the form and manner required. The mixtures can be dispersed in water with the aid of a wetting agent or they can be employed in organic liquid compositions, oil and water, water in oil emulsions, with or without the addition of wetting, dispersing or emulsifying agents. An herbicidally effective amount depends upon the nature of the seeds or plants to be controlled and the rate of application varies from 0.5 to approximately 50 pounds per acre.

The phytotoxic compositions of this invention employing an herbicidally effective amount of the compounds described herein are applied to the plants in the conventional manner. Thus, the dust and liquid compositions can be applied to the plants by the use of power-dusters, boom and hand sprayers and spray-dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions be admixed with the soil particles, since these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

What is claimed is:

1. A compound having the formula

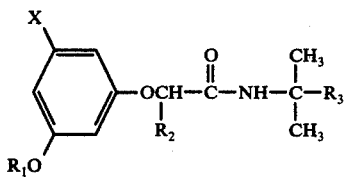

in which X is a halogen, $R_1$ is lower alkyl, $R_2$ is lower alkyl and $R_3$ is lower alkyl, or lower alkynyl.

2. A compound according to claim 1 in which X is chloro.

3. A compound according to claim 1 in which $R_1$ is methyl.

4. A compound according to claim 1 in which $R_2$ is ethyl.

5. A compound according to claim 1 in which $R_3$ is lower alkyl.

6. A compound according to claim 1 in which $R_3$ is lower alkynyl.

7. A compound according to claim 1 in which X is chloro, $R_1$ is methyl, $R_2$ is ethyl and $R_3$ is ethynyl.

8. A compound according to claim 1 in which X is chloro, $R_1$ is methyl, $R_2$ is ethyl and $R_3$ is methyl.

9. A method for controlling undesirable vegetation comprising applying to said vegetation or the locus thereof an herbicidally effective amount of a compound having the formula

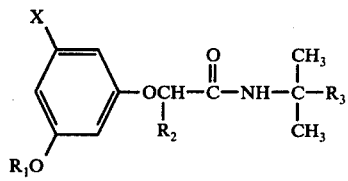

in which X is a halogen, $R_1$ is lower alkyl, $R_2$ is lower alkyl and $R_3$ is lower akyl, or lower alkynyl.

10. A method according to claim 9 in which X is chloro, $R_1$ is methyl and $R_2$ is ethyl.

11. An herbicidal composition of matter comprising: (a) an herbicidally effective amount of a compound having the formula

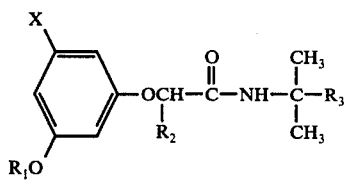

in which X is a halogen, $R_1$ is lower alkyl, $R_2$ is lower alkyl and $R_3$ is lower alkyl, or lower alkynyl; and (b) an inert carrier or diluent.

* * * * *